United States Patent [19]

Navarrini et al.

[11] Patent Number: 5,235,074
[45] Date of Patent: Aug. 10, 1993

[54] HALOGENATED 1,3-DIOXOLANES

[75] Inventors: Walter Navarrini; Simonetta Fontana; Vittorio Montanari, all of Milan, Italy

[73] Assignee: Ausimont S.p.A., Italy

[21] Appl. No.: 847,138

[22] Filed: Mar. 6, 1992

Related U.S. Application Data

[62] Division of Ser. No. 711,775, Jun. 7, 1991.

[30] Foreign Application Priority Data

Jun. 7, 1990 [IT] Italy .................. 20578 A/90

[51] Int. Cl.$^5$ .................................... C07D 317/16
[52] U.S. Cl. .................................. 549/449; 549/450; 549/455
[58] Field of Search ............. 549/450, 449, 455

[56] References Cited

U.S. PATENT DOCUMENTS

| | | | |
|---|---|---|---|
| 4,393,227 | 7/1983 | Squire | 549/455 |
| 4,429,143 | 1/1984 | Anderson et al. | 549/455 |
| 4,485,250 | 11/1984 | Squire | 549/455 |
| 4,535,175 | 8/1985 | Squire | 549/455 |
| 4,810,806 | 3/1989 | Krespan | 549/455 |
| 4,908,461 | 3/1990 | Hung | 549/455 |
| 4,973,714 | 11/1990 | Krespan | 549/455 |

FOREIGN PATENT DOCUMENTS

| | | | |
|---|---|---|---|
| 0750403 | 1/1967 | Canada | 549/449 |
| 0196693 | 10/1986 | European Pat. Off. | 549/450 |
| 9104251 | 4/1991 | PCT Int'l Appl. | |
| 1051648 | 12/1966 | United Kingdom | 549/450 |
| 1189337 | 4/1970 | United Kingdom | 549/450 |
| 2211845 | 7/1989 | United Kingdom | 549/455 |

OTHER PUBLICATIONS

"Some Reactions of Bis(fluoroxy)difluoromethane, $CF_2(OF)_2$", pp. 624-626 F. A. Hohorst, et al., *Inorg. Chem.*, vol. 7, No. 3, (Mar. 1968).

*Primary Examiner*—C. Warren Ivy
*Assistant Examiner*—A. A. Owens
*Attorney, Agent, or Firm*—Morgan & Finnegan

[57] ABSTRACT

This invention process for preparing 1,3-dioxanes of formula:

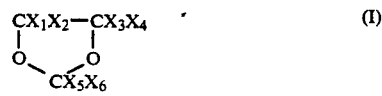

wherein;

$X_1$, $X_2$, $X_3$ and $X_4$, like or different from one another, represent F, Cl, Br, I, $CF_2OSO_2F$, $SO_2F$, $C(O)F$, H, perhaloalkyl or oxyperhaloalkyl radicals containing from 1 to 5 carbon atoms, $X_5$ and $X_6$, like or different from each other, represent F or $CF_3$. Said process is characterized in that a bis(-fluoroxy)perfluoroalkane is reacted, at a temperature ranging from $-140°$ C. to $+60°$ C., with a halogenated olefin.

This invention also relates to new 1,3-dioxolanes of formula (I) belonging to the class defined hereinbefore.

5 Claims, No Drawings

HALOGENATED 1,3-DIOXOLANES

This is a divisional of co-pending application Ser. No. 07/711,775 filed Jun. 7, 1991.

FIELD OF THE INVENTION

The present invention relates to a process for preparing halogenated 1,3-dioxolanes and new halogenated 1,3-dioxolones.

More particularly, the present invention relates to the preparation of halogenated 1,3-dioxolanes having formula:

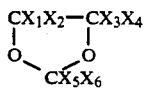  (I)

wherein:
$X_1$, $X_2$, $X_3$ and $X_4$, like or different from one another, represent F, Cl, Br, I, $CF_2OSO_2F$, $SO_2F$, $C(O)F$, H, perhaloalkyl or oxyperhaloalkyl radicals containing from 1 to 5 carbon atoms,
$X_5$ and $X_6$, like or different from each other, represent F or $CF_3$.

BACKGROUND OF THE INVENTION

According to the art, halogenated 1,3-dioxolanes are prepared starting from complex reagents or using industrially onerous multistage processes, which provide often low or not constant yields, as is better explained later on.

German patent application No. 2,604,350 teaches the synthesis of halogenated 1,3-dioxolanes by fluorination of the corresponding ethylcarbonate with $SF_4+HF$ (or $TiF_4$).

Published European patent application No. 80,187 describes the synthesis of perfluoro-1,3-dioxole and of its polymers via dechlorination of the corresponding 4,5-dichloro-dioxolane, prepared starting from ethylene carbonate by photochemical chlorination with $Cl_2$ and subsequent fluorination with $SF_4+HF$ and with $SbF_3$ (or HF)+$SbCl_5$; The yields of said last step can also be greater than 90%, but they are not reproducible.

The abovesaid 4,5-dichlorodioxolane is also prepared from 1,3-dioxolane by photochemical chlorination with $Cl_2$ and fluorination with $SbF_3$ (or HF)+$SbCl_5$; However, the total yield does not exceed 7%.

U.S. Pat. No. 2,925,424 describes how to synthesize halogenated 1,3-dioxolanes by reacting a perhaloketone with a 2-haloethanol.

In U.S. Pat. Nos. 3,865,845 and 3,978,030, fluorinated dioxoles and homopolymers and copolymers thereof are prepared by dehalogenizing dioxolanes with two vicinal halogens, prepared according to the method described in the above-cited U.S. Pat. No. 2,925,424.

European patent applications Nos. 76,581 and 301,881 describe the condensation of a fluorinated ketoester with a 2-haloethanol or an ethylene oxide in order to obtain halogenated 1,3-dioxolanes.

U.S. Pat. No. 3,699,145 describes the photo-oxidation of perfluoropropene with molecular oxygen whereby it is possible to obtain, along with various straight perfluoropolyethers, low amounts of perfluoro-4-methyl-1,3-dioxolane and of perfluoro-2,4-dimethyl-1,3-dioxolane.

In Journal of Fluorine Chemistry 12 (1978), pages 23–29, the reaction of bis(fluoroxy-difluoromethane with the Dewar hexafluorobenzene is described. It is expressly stated that, although the perfluorocycloolefins are generally not reactive towards bis(fluoroxy)difluoromethane, in the case of the Dewar hexafluorobenzene, along with polymeric products, oxiranic products and products resulting from a simple fluorination of the double bond, there are obtained, with low yields, products having a dioxolane structure. The higher reactivity is attributable to its particular dicyclic structure, which exhibits olefinic bonds with anomalous angles.

Lastly, Organic Chemistry 3 (1986), 624–6, describes the reaction of bis(fluoroxy)difluoromethane (hereinafter briefly referred to as "BDM") with two particular olefins: tetrafluoroethylene and trans-1,2-dichloroethylene.

When it is operated with tetrafluoroethylene, a mixture of the olefin, diluted in a nitrogen excess, is fed to BDM at a temperature of $-184°$ C.; at said temperature, the reagents are in the solid state. Alternatively, the olefin and the BDM are condensed together in the reaction vessel at $-184°$ C. In both cases, not the corresponding 1,3-dioxolane but the addition product of formula $CF_2(OCF_2—CF_3)_2$ is obtained.

In the reaction with trans-1,2-dichloroethylene it is operated, according to the above-cited article, by condensing the olefin with a solvent and the BDM in the reaction vessel at a temperature of $-184°$ C. and then allowing the whole to stand for a few days at room temperature. Also in this case, not the corresponding 1,3-dioxolane, but the straight compound of formula $CF_2(OCH—CHClF)_2$ is obtained.

Thus, from the examined art, it is apparent that up to the date of the present invention it was not known to prepare 1,3-dioxolanes by direct reaction of olefins with bis(fluoroxy)perfluoroalkanes, and only a limited number of halogenated 1,3-dioxolanes could be prepared by means of complicated processes and with not always satisfactory and reproducible yields.

DESCRIPTION OF THE INVENTION

It is an object of the present invention to provide a single-stage process for preparing 1,3-dioxolanes of formula (I), which does not exhibit the limitations and the drawbacks affecting the processes of the art.

Another object of the present invention is to provide new halogenated 1,3-dioxolanes.

Thus, an object of the present invention is process for preparing halogenated 1,3-dioxolanes of formula (I) wherein:
$X_1$, $X_2$, $X_3$ and $X_4$, like or different from one another, represent F, Cl, Br, I, $CF_2OSO_2F$, $SO_2F$, $C(O)F$, H, perhaloalkyl or oxyperhaloalkyl radicals containing from 1 to 5 carbon atoms,
$X_5$ and $X_6$, like or different from each other, represent F or $CF_3$,
characterized in that a bis(fluoroxy)perfluoroalkane of formula $C(OF)_2X_5X_6$ is reacted, at a temperature ranging from $-140°$ to $+60°$ C., with a halogenated olefin of formula $CX_1X_2=CX_3X_4$, $X_1$, $X_2$, $X_3$, $X_4$, $X_5$ and $X_6$ being the same as defined hereinbefore.

In a preferred embodiment of the invention, a flow of a bis(fluoroxy)perfluoroalkane, preferably in the presence of an inert diluting gas, and optionally also a gaseous or liquid stream consisting of a halogenated olefin, are fed into a liquid phase consisting of a halogenated olefin and of a solvent, if any, maintained at the above-cited reaction temperature.

As an alternative, the halogenated olefin and the bis(fluoroxy)perfluoroalkane are simultaneously fed into a vessel containing the optional solvent.

At the end of the reaction time, feeding of the reagents is stopped. The reaction products are separated from the solvent, if any, and from the unreacted olefin, if present, preferably by fractionated distillation.

The reaction can be conducted also in a thoroughly continuous manner by continuously withdrawing a liquid phase portion from the reactor, from this phase the reaction products are separated and recovered, while the optional solvent and the unreacted olefin are recycled.

The total pressure in the reaction environment preferably ranges from 1 to 10 kg/cm$^2$ abs.

More usually, it is operated at about the atmospheric pressure.

The inert diluting gas of bis(fluoroxy)perfluoroalkane when it is utilized, is selected for example from nitrogen, argon, helium, $CF_4$ and $C_2F_6$.

A further embodiment of the present invention consists in a particular discontinuous process for preparing halogenated 1,3-di oxolanes of formula (I), wherein:

$X_1$, $X_2$, $X_3$ and $X_4$, like or different from one another, represent F, Cl, Br, I, $CF_2OSO_2F$, $SO_2F$, C(O)F, H, perhaloalkyl or oxyperhaloalkyl radicals containing from 1 to 5 carbon atoms, $X_5$ and $X_6$, like or different from one another, represent F or $CF_3$, characterized in that a bis(fluoroxy)perfluoroalkane of formula $C(OF)_2X_5X_6$ is reacted, at a temperature ranging from $-140°$ C. to $+60°$ C., with a halogenated olefin of formula $CX_1X_2=CX_3X_4$, $X_1$, $X_2$, $X_3$, $X_4$, $X_5$ and $X_6$ being the same as defined hereinbefore, on condition that at least one from among $X_1$, $X_2$, $X_3$ and $X_4$ is F.

In the discontinuous method the reagents are condensed at a temperature not exceeding $-140°$ C. in the reaction vessel, preferably along with a solvent.

The abovesaid condensation is preferably conducted at a temperature of $-196°$ C.

The reaction vessel so charged is usually allowed to reach the desired reaction temperature and is maintained at this temperature for a time ranging from 1 hour to 24 hours.

The reaction products are purified by vacuum distillation by causing the vapors to flow through cooled traps.

It must be pointed out that the temperature at which the reagents are condensed in the reaction vessel is not the actual reaction temperature, but only a convenient experimental procedure for charging the reagents in a discontinuous and exact manner without letting them react until reaching the desired reaction temperature.

In the discontinuous method the pressure preferably ranges from 0.5 to 20 kg/cm$^2$ abs.

In both processes the reaction can be conducted in a condensed phase or in a gas phase.

The synthesis of bis(fluoroxy)perfluoroalkanes of formula:

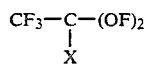

wherein X is F or $CF_3$, is described in JACS (1967), 2263 and in U.S. Pat. No. 3,420,866.

Among the utilized bis(fluoroxy) perfluoroalkanes, bis(fluoroxy) difluoromethane (BDM) is particularly preferred.

The synthesis of BDM is described in JACS (1967), 1809-10.

The halogenated olefins utilized in the present invention preferably contain from 2 to 6 carbon atoms.

Particularly preferred olefins are, for example: CFCl=CFCl, CFBr=CFBr, $CF_2$=CFBr, $CF_2$=CH—$CF_3$, $CF_2$=CF—$SO_2F$, $CF_2$=CF—$CF_2$—$OSO_2F$, $CF_2$=CF—C(O)F, $CF_2$=CF—$CF_3$, $CF_2$=CF—O—$CF_2$—$CF_3$.

The reaction temperature for both processes is usually in the range from $-140°$ to $+60°$ C.; preferably it ranges from $-100°$ to $+30°$ C.

The solvent, when it is utilized, is preferably selected from straight and cyclic fluorocarbons, chlorofluorocarbons, perfluoroamines and perfluorinated ethers.

Examples of suitable fluorocarbons and chlorofluorocarbons are: perfluorocyclobutane, perfluorocyclohexane, 1-chloropentafluoroethane, 1,1,2-trichloro-1,2,2-trifluoroethane, 1,2-dichlorotetrafluoroethane and 1,1,1-trifluorotrichloroethane.

Examples of suitable perfluoroamines are the perfluoroaminic Fluorinert ® produced by 3M Co.

Examples of suitable perfluorinated ethers are the perfluoropolyethers having a boiling point lower than 250° C., such as the Gladen ® produced by Montefluos.

The halogenated olefin concentration in the liquid phase generally ranges from 0.01 to 10 moles/liter and above, i.e. up to the molar concentrations of the haloolefins in the pure state.

A further objects of the present invention are new 1,3-dioxolanes of formula (I), wherein: $X_1$, $X_2$, $X_3$ and $X_4$, like or different from one another, represent F, Cl, Br, I, $CF_2OSO_2F$, $SO_2F$, C(O)F, H, perhaloalkyl or oxyperhaloalkyl radicals containing from 1 to 5 carbon atoms, $X_5$ and $X_6$, like or different from each other, represent F or $CF_3$, on condition that at least one from among $X_1$, $X_2$, $X_3$ and $X_4$ is Br, I, $CF_2OSO_2F$, $SO_2F$, C(O)F, a perhaloalkyl or oxyperhaloalkyl radical containing from 1 to 5 carbon atoms and furthermore that, when one from among $X_1$, $X_2$, $X_3$ and $X_4$ is $CF_3$, at least one among the other three is different from F, or $X_5$ and $X_6$ are $CF_3$, and when one from among $X_1$, $X_2$, $X_3$ and $X_4$ is Br or I, the other three are F, or at least one among $X_5$ and $X_6$ is F.

The abovesaid 1,3-dioxolanes are preparable according to the process of the present invention by reacting, at a temperature ranging from $-140°$ C. to $+60°$ C., a bis(fluoroxy)perfluoroalkane of formula $C(OF)_2X_5X_6$ with a halogenated olefin of formula $CX_1X_2=CX_3X_4$, where for $X_1$, $X_2$, $X_3$, $X_4$, $X_5$ and $X_6$ the above-listed conditions are valid.

The starting halogenated olefin of formula $CX_1X_2=CX_3X_4$ preferably contains at least two, and more preferably at least three F atoms among the substituents $X_1$, $X_2$, $X_3$ and $X_4$.

Furthermore, in the starting bis(fluoroxy)perfluoroalkane of formula $C(OF)_2X_5X_6$, $X_5$ and $X_6$ are preferably F.

The resulting 1,3-dioxanes can be utilized as fluorinated fluids, for example as an alternative to the chlorofluorocarbons available on the market.

They are also used as general anaesthetics.

A few halogenated 1,3-dioxolanes comprised in general formula (I), which are an object of the present invention, are listed in Table 1.

The dioxolanes marked with an asterisk are covered by the general formula of the new 1,3-dioxolanes object of the present invention.

TABLE 1

| $X_1$ | $X_2$ | $X_3$ | $X_4$ | $X_5$ | $X_6$ | Exam. No. | DIOXOLANE |
|---|---|---|---|---|---|---|---|
| F | F | F | $SO_2F$ | F | F | 1 | (1)* |
| F | F | F | $CF_2OSO_2F$ | F | F | 2 | (2)* |
| F | F | F | $C(O)F$ | F | F | 3 | (3)* |
| F | F | F | $CF_3$ | F | F | 4 | (4) |
| F | F | F | $OCF_2CF_3$ | F | F | 5 | (5)* |
| F | F | F | Br | F | F | 6 | (6)* |
| F | F | H | $CF_3$ | F | F | 7 | (7)* |
| F | F | F | Cl | F | F | 8 | (8) |
| F | F | F | $CF_3$ | $CF_3$ | F | 9 | (9) |
| F | F | F | F | F | F | 10 | (10) |
| Cl | Cl | Cl | Cl | F | F | 11-12 | (11) |

EXAMPLES

For a better understanding of the possibilities of carrying into effect the present invention, a few illustrative but not limitative examples are given hereinafter.

EXAMPLE 1

2,2,4,5,5-pentafluoro-4-fluorosulphonyl-1,3-dioxolane (1)

In a Pyrex glass flask having a volume of 50 ml, equipped with a PTFE valve and connected to a vacuum pipe, 2.0 m.moles of distilled $CF_2$=$CF$—$SO_2F$, 2.0 m.moles of chlorotrifluoromethane and 1.0 m.moles of bis-fluoroxy-difluoromethane were condensed in succession at the temperature of liquid nitrogen. The reaction flask was placed into a Dewar vessel containing solid $CFCl_3$ and liquid nitrogen. After 16 hours, the temperature in the Dewar vessel was of $-20°$ C. Now the reaction flask was further cooled in liquid nitrogen, it was connected to the vacuum pipe and was allowed to reach again the room temperature while fractionating the vapors through traps cooled to $-80°$ C., $-110°$ C. and $-196°$ C. The trap at $-80°$ C. contained 0.46 m.moles of 2,2,4,5,5-pentafluoro-4-fluorosulphonyl-dioxolane identified by means of NMR and mass spectroscopy.

The trap at $-110°$ C. contained 2.10 m.moles of a mixture of $CFCl_3$, of dioxolane (1) and of $CF_3CF_2SO_2F$ as determined by means of NMR and IR spectroscopy.

The trap at $-196°$ C. contained 1.90 m.moles of a mixture of $COF_2$, $CFCl_3$ and $CF_3CF_2SO_2F$ according to the IR spectrum.

The content of the trap at $-110°$ C. was fractionated again through traps maintained at $-90°$ C., $-100°$ C. and $-196°$ C.: in the first two traps, further 0.14 m.moles of dioxolane (1) were recovered.

The dioxolane (1) yield, defined as the ratio between the moles of dioxolane (1) and the utilized moles of BDM, was equal to 60%.

Characterization of dioxolane (1)

NMR $^{19}F$ spectrum in p.p.m. relating to $CFCl_3$=0: +45.6 (1F, $SO_2F$); $-54.1$ and $-56.7$ (2F, $OCF_2O$); $-78.3$ and $-83.2$ (2F, $OCF_2CF$); $-109.6$ (1F, CF).

Mass spectrum (electronic impact), main peaks and relevant intensities: 69 (86%); 97 (100%); 135 (4%); 163 (25%).

Infrared spectrum, main absorption bands (cm$^{-1}$): 1474, 1356, 1259, 1178.

EXAMPLE 2

2,2,4,5,5-pentafluoro-4-(difluoro-fluorosulphonyloxy)-methyl dioxolane (2)

3.5 m.moles of $CF_2$=$CF$—$CF_2$—$OSO_2F$, 7.7 m.moles of $CFCl_3$, 1.75 m.moles of bis-fluoroxydifluoromethane were successively condensed in a Pyrex glass flask, having a volume of 50 ml and equipped with a PTFE valve, at the temperature of liquid nitrogen. The reaction flask was put into a Dewar vessel containing solid $CFCl_3$ and liquid nitrogen. After 16 hours, the temperature was equal to $-10°$ C. The flask was allowed to reach again the room temperature in 1 hour. The vapors were fractionated in a vacuum of $10^{-3}$ mm Hg by means of traps maintained at $-60°$ C., $-90°$ C. and $-196°$ C. The trap at $-60°$ C. contained 1.14 m.moles of dioxolane (2) identified by its NMR signals and by the mass spectrum. The trap at $-90°$ C. contained 6.43 m.moles of $CFCl_3$ and of $CF_3CF_2CF_2OSO_2F$ identified by the NMR spectrum.

The trap at $-110°$ C. contained 2.73 m.moles of $CFCl_3$ identified by infrared spectrum. The trap at $-196°$ C. contained 0.95 m.moles of $CFCl_3$ and traces of bisfluoroxydifluoromethane, as is revealed by IR spectroscopy.

The dioxolane (2) yield defined as in example 1 was equal to 65%.

Characterization of dioxolane (2)

NMR $^{19}F$ spectrum in p.p.m. relating to $CFCl_3$=0 +50.3 (1F, $OSO_2F$); $-54.8$ and $-58.3$ (2F, $OCF_2O$); $-81.3$ and $-84.8$ (2F, $OCF_2CF$); $-83.7$ (2F, $CF_2O$-$SO_2F$); $-127.0$ (1F, CF).

Mass spectrum (electronic impact), main peaks and relevant intensities: 293 (<1%); 227 (<1%); 213 (<1%); 149 (37%); 119 (62%); 97 (86%); 83 (65%); 69 (100%); 47 (62%).

Infrared spectrum, main absorption bands (cm$^{-1}$): 1502, 1360, 1263, 1180.

EXAMPLE 3

2,2,4,5,5-pentafluoro-4-fluorocarbonyl-1,3-dioxolane (3)

Into a Pyrex glass flask of 50 ml volume, equipped with a PTFE valve, 6 ml of FC75 were introduced, vacuum was created to remove the dissolve air, and 2 m.moles of perfluoroacryloyl fluoride were condensed. The reactor was closed, brought to room temperature and repeatedly stirred. The reactor was then cooled to $-196°$ C. and 1 m.mole of BDM was charged through condensation. The reaction flask so charged was placed into a Dewar vessel containing solid $CFCl_3$ and liquid nitrogen. After 16 hours the temperature was of $-10°$ C. The flask was caused to reach again the room temperature in 1 hour.

The vapors were fractionated in a vacuum of $10^{-3}$ mm Hg by means of traps maintained at $-50°$ C., $-110°$ C. and $-196°$ C. The trap at $-50°$ C. contained FC-75, the trap at $-110°$ C. contained 0.55 m.moles of (3), identified by the signals in the NMR spectrum and by the infrared spectrum, particularly by the band at 1889 cm$^{-1}$.

The trap at $-196°$ C. contained 1.4 m.moles of $CF_3CF_2C(O)F$ along with traces of BDM, $COF_2$ and product (3), identified by the infrared spectrum and NMR spectrum.

The dioxolane (3) yield defined as in example 1 was equal to 55%.

Characterization of dioxolane (3)

NMR $^{19}F$ spectrum in p.p.m. relating to $CFCl_3=0$ +24.2 (1F, C(O)F); −53.1 and −58.6 (2F, $OCF_2O$); −77.8 and −88.8 (2F, $OCF_2CF$); −118.6 (1F, CF).

Infrared spectrum, main bands: 1889, 1256, 1181.

EXAMPLE 4

2,2,4,5,5-pentafluoro-4-trifluoromethyl-1,3-dioxolane (4)

In a steel cylinder having a volume of 75 ml there were condensed, at the temperature of liquid nitrogen, 4 m.moles of perfluoropropene followed by 12 m.moles of $CF_2Cl_2$ (FC-12), reaction solvent, and the same was brought again to room temperature to favor the mixing of solvent and perfluoropropene. Then, always at the temperature of liquid nitrogen, further 4 m.moles of FC-12 and 2 m.moles of BDM were condensed in the cylinder, and the reaction temperature was raised very slowly up to room temperature in a time of 24 hours. The content was then gathered in a trap, placed in liquid nitrogen, of a conventional vacuum pipe, and then measured: reaction products and solvent amounted to 20.1 m.moles. The gas-chromatographic analysis, together with the weight balance, of the reaction mixture indicated a dioxolane (4) yield, defined as in example 1, of 95%. $^{19}F$ NMR was in accordance with the data reported in literature.

EXAMPLE 5

2,2,4,5,5-pentafluoro-4-perfluoroethoxy-1,3-dioxolane (5)

In a steel cylinder having a volume of 300 ml there were condensed 12.0 m.moles of perfluoroethoxy-perfluoroethylene and 120 ml of $CF_2Cl_2$ (FC-12), reaction solvent, at the temperature of liquid nitrogen, then the cylinder was brought again to room temperature. In the same cylinder there were subsequently condensed further 5 m.moles of FC-12 and 6 m.moles of BDM, always at the liquid nitrogen temperature, and the temperature in the reactor so charged was then gradually raised to room temperature in a time of 24 hours. The cylinder content was then distilled very slowly in a conventional vacuum pipe through traps maintained at temperatures of −196° C., −120° C., −100° C., −50° C.; in the trap at −196° C. there was mainly recovered FC-12, in the trap at −120° C. there were recovered 32.4 m.moles of a mixture containing 73.7% of FC-12 (GLC), 19% of perfluorodiethylether (GLC) and 3.4% of dioxolane (5) (GLC), in the trap at at −100° C. there were recovered 1.22 g of a mixture containing 73% (GLC) of (5). The content of said last trap was distilled again further two times through traps maintained at −60° C. and −100° C. until (5) was obtained with a purity higher than 92%.

The dioxolane (5) yield, defined as for example 1, was equal to 68%. The reaction products were characterized by means of gas chromatography, mass spectrometry, $^{19}F$ NMR spectrometry and IR spectrometry.

Characterization of dioxolane (5)

Mass spectrum (electronic impact), main peaks and relevant intensities: 163 (10%); 135 (1,8%); 119 (100%); 116 (31%); 97 (47%); 69 (50%); 69 (50%); 47 (35%).

$^{19}F$-NMR in p.p.m. from $CFCl_3=0$

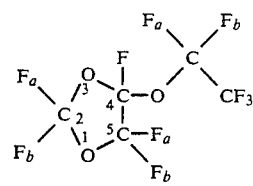

2-$CF_2$: $\delta_a = -56.17$, $\delta_b = -57.43$; 5-$CF_2$: $\delta_a = -83.36$, $\delta_b = -88.85$; 4-CF: $\delta = -85.51$; $CF_3$: $\delta = -87.07$; $CF_2$: $\delta_a = -87.99$, $\delta_b = -89.34$;

IR, main bands (cm$^{-1}$): 1248, 1209, 1153, 1103, 1023, 717.

EXAMPLE 6

4-bromo-2,2,4,5,5-pentafluoro-1,3-dioxolane (6)

Into a multineck glass reactor equipped with: magnetic entrainment mechanical stirrer, reflux cooler, thermocouple, inner plunging pipes for introducing the reagents, and maintained at a temperature of −70° C., there were simultaneously fed—after having introduced 75 ml of dichlorodifluoromethane—0.75 l of bis(-fluoroxy)difluoromethane at a flowrate of 0.375 l/h diluted with $N_2$ (0.5 l/h) and bromotrifluoroethylene (5.4 g/h) for 2 hours.

The gas-chromatographic analysis of the rough reaction product (column thickness 1000, from 50° C. to 200° C., 10° C/min.) revealed that the main reaction products: bromotrifluor-oxirane, bromopentafluoroethane, dioxolane (6) and 1,1,2-tribromo-1,2,2-trifluoroethane, were present in the following ratio, respectively: 10%, 41.8%, 46.6% and 1.6%. Then, after stripping of most of the solvent and of a part of the low-boiling products such as oxirane and bromopentafluoroethane, said rough reaction product was distilled on a tray column, Spaltrohr Fisher, at atmospheric pressure.

The fraction having a boiling point ranging from 58° C. to 63° C. was collected; it consisted of 6.6 g of dioxolane (6).

The dioxolane (6) yield, defined as in example 1, was of 81%.

Characterization of dioxolane (6)

$^{19}F$ NMR spectrum, in p.p.m. from $CFCl_3O=0$: −55 (1F, $OCF_2O$), −58 (1F, $OCF_2O$); −63 (1F, CFBr), −12.2 (1F, $CF_2$), −91 (1F, $CF_2$).

Mass spectrum (electronic impact), main peaks and relevant intensities: 97 (100%), 163 (45%), 69 (38%), 47 (31%), 50 (19%).

EXAMPLE 7

2,2,5,5-tetrafluoro-4-trifluoromethyl-1,3-dioxolane (7)

In a steel cylinder of 75 ml volume there were condensed, at the temperature of liquid nitrogen, 10 m.moles of $CF_2Cl_2$ (FC-12), reaction solvent, and 3.0 m.moles of 1,1,3,3,3-pentafluoropropene, then the cylinder was brought again to room temperature in order to permit the mixing of 1,1,3,3,3-pentafluoropropene and solvent.

In the same cylinder, cooled again in liquid nitrogen, there were then condensed, in the order, further 5 m.moles of FC-12 and 1.50 m.moles of BDM and the reaction temperature was gradually raised to room temperature in a time of 24 hours. The content was distilled in a conventional vacuum pipe through traps maintained at −80° C., −120° C., −196° C.; in the trap at −196° C. there were recovered 15.2 m.moles of a mixture having the following composition (GLC): 95.4% of FC-12 and 4.3% of 1,1,1,2,3,3,3-heptafluoropropane, while at −120° C. there were recovered 0.158 g of a mixture having the following composition: 21.6% of FC-12, 44.8% of 1,1,1,2,3,3,3-heptafluoropropane, 25.9% of (7), and at −80° C. there were recovered 0.227 g of a mixture having composition: 1.7% of 1,1,1,2,3,3,3-heptafluoropropane and 50.7% of (7).

(7) was characterized by means of mass spectrometry.
The calculated (7) yield was of 48%.
Characterization of dioxolane;
Mass spectrum (electronic impact), main peaks and relevant intensities: 195 (2.6%); 175 (12.7%); 167 (9.4%); 148 (20.8%); 145 (29.9%); 129 (10.7%); 101 (22.1%); 79 (31.9%); 69 (100%); 51 (59.3%); 47 (20.1%).

$^{19}$F NMR in p.p.m. from CFCl$_3$=0:

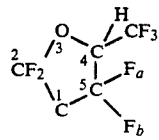

2-CF$_2$: δ= −55.59; 5-CF$_2$: δ$_a$= −66.41; δ$_b$= −84.33; CF$_3$: δ= −76.31 complex doublet.

H$^1$-NMR in p.p.m. from (CH$_3$)$_4$Si=0: 5.03 complex signal.

IR, main bands (cm$^{-1}$): 2988, 1396, 1360, 1326, 1285, 1251, 1213, 1192, 1128, 963, 895, 853, 744, 702.

EXAMPLE 8

4-cloro-2,2,4,5,5-pentafluoro-1,3-dioxolane (8)

Into a glass reactor equipped with: mechanical stirrer, reflux cooler, thermocouple, inner plunging pipes for introducing the reagents, and maintained at a temperature of −75° C., there were introduced 75 ml of dichlorodifluoromethane and 10 g of chlorotrifluoroethylene. Then 0.91 of bis(fluoroxy)difluoromethane at a flowrate of 0.4 l/h diluted with N$_2$ (0.5 l/h) were fed into the reactor.

At the end of the reaction, after having removed by distillation the chloropentafluoroethane, most of the solvent and the non-reacted chlorotrifluoroethylene, 12 g of a mixture were recovered containing 52% of dioxolane (8) in dichloro-difluorometano (GLC).

By distillation through cooled traps kept under vacuum, 5.2 g of dioxolane (8) were collected.

The dioxolane (8) yield, defined as in example 1, was equal to 65%.

Characterization of dioxolane (8)

NMR $^{19}$F spectrum in p.p.m. relating to CFCl$_3$=0−55 (1F, OCF$_2$O); −58 (1F, OCF$_2$O); −69 (1F, CFCl); −76 (1F, CF$_2$); −91 (1F, CF$_2$).

Mass spectrum (electronic impact), main peaks and relevant intensities: 66(82%); 69(86%); 97(100%) 116(68%); 132(38%); 163(92%); 179(1%).

EXAMPLE 9

2,4-bis(trifluoromethyl)-2,4,5,5-tetrafluoro-1,3-dioxolane (9)

Into a multineck glass reactor of 200 ml volume equipped with: mechanical stirrer, reflux cooler kept at the temperature of −78° C., thermocouple, inner plunging pipes for introducing the reagents, and maintained at a temperature of −70° C., there were introduced 100 ml of dichlorodifluoromethane and 20 g of perfluoropropene. Then, there was fed a mixture of hypofluorites containing 70% of CF$_3$CF(OF)$_2$, 7.3% of CF$_3$CF$_2$OF and 2.2% of CF$_3$OF diluted with helium (5 l/h) for 3.5 hours.

The above mixture of hypofluorites was prepared according to the method described in Journal of Organic Chemistry 51,9 (1986), page 1485, i.e. feeding in a continuous manner a flow of F$_2$ at a flowrate of 0.5 l/h diluted with helium (5 l/h) on a bed of sodium trifluoroacetate (25 g) maintained at a temperature of −40° C.

From the rough reaction product, after stripping of the solvent, of the non-reacted perfluoropropene and of the low-boiling products such as, for example, CF$_3$CF$_2$CF$_3$ and CF$_3$OCF$_2$CF$_2$CF$_3$, 4,6 g of a mixture were recovered containing 72.5% of dioxolane (9) (GLC/MS), 10.7% of CF$_3$CF$_2$OCF(CF$_3$)$_2$ (GLC/MS) and 16.6% of CF$_3$CF$_2$OCF$_2$CF$_2$CF$_3$ (GLC/MS).

By preparative gas-chromatography, 2.1 g of dioxolane (9) were collected.

The dioxolane (6) yield, defined as in example 1, was equal to 14%.

Characterization of dioxolane (9)

NMR $^{19}$F spectrum in p.p.m. relating to CFCl$_3$=0

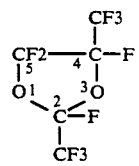

—CF3= −82.5 ppm, —CF= −89.4 ppm, —CF= −12.1 ppm, —CF3= −81.7 ppm, —CF2= −85.3ppm.

Mass spectrum (electronic impact), main peaks and relevant intensities: relative: 263 (21%); 213(100%); 169(49%); 147(35%); 119(82%); 97(68%); 59(66%).

EXAMPLE 10 perfluoro-1,3-dioxolane (10)

Into a multineck glass reactor equipped with: magnetic entrainment mechanical stirrer, reflux cooler, thermocouple, inner plunging pipes for introducing the reagents, and maintained at a temperature of −80° C., there were simultaneously fed-after having introduced 75 of FC 75-0.5 l of bis(fluoroxy)difluoromethane at a flowrate of 0.3 l/h diluted with N$_2$ (0.5 l/h) and 5.0 g of tetrafluoroethylene (3.0 g/h).

The gas-chromatographic analysis of the rough reaction product (column thickness 1000, from 50° C. to 200° C., 10° C./min.) revealed that the main reaction products: perfluoro-1,3-dioxolane, perfluoroethane and perfluorocyclobuthane were present in the following ratios, respectively: 46%, 47% and 7%.

The dioxolane (10) yield, defined as in example 1, was of 56%.

Characterization of dioxolane (10)

Mass spectrum (electronic impact), main peaks and relevant intensities: 50(100%), 69(22%), 97(15%), 116(17%), 163(1%).

EXAMPLE 11

4,4,5,5,-tetrachloro-2,2-difluoro-1,3-dioxolane (11)

Into a multineck glass reactor of 100 ml volume equipped with: magnetic entrainment mechanical stirrer, reflux cooler, thermocouple, inner plunging pipes for introducing the reagents, and maintained at a temperature of $-76°$ C., there were introduced 75 ml of dichlorodifluoromethane and 15 g of tetrachloroethylene. Then 1.00 l of bis(fluoroxy)difluoromethane at a flowrate of 0.3 l/h diluted with $N_2$ (0.5 l/h) were fed into the reactor.

At the end of the reaction, after having removed the solvent by distillation, 16.3 g of a mixture were recovered. The gas-chromatographic analysis (column thickness 1000, from 50° C. to 180° C.) revealed that said mixture contained 50.3% of the dioxolane (11) and 43% of 1,2-difluorotetrachloroethane.

The dioxolane (11) yield, defined as in example 1, was of 74%.

Characterization of dioxolane (11)

$^{19}F$ NMR spectrum, in p.p.m. from $CFCl_3O=0$: $-47$ (2F, $OCF_2O$).

Mass spectrum (electronic impact), main peaks and relevant intensities: 47(30%), 82(60%), 119(52%), 145(100%), 166(31%), 213(32%).

EXAMPLE 12

4,4,5,5,-tetrachloro-2,2-difluoro-1,3-dioxolane (11)

Into a multineck glass reactor of 350 ml volume equipped with: magnetic entrainment mechanical stirrer, reflux cooler, thermocouple, inner plunging pipes for introducing the reagents, and maintained at a temperature of $-40°$ C., there were introduced 50 ml of $CFCl_3$ and 182 g of tetrachloroethylene. Then 0.6 moles of bis(fluoroxy)difluoromethane at a flowrate of 0.8 l/h di diluted with $N_2$ (0.5 l/h) were fed, into the reactor.

At the end of the reaction, after having removed the solvent by distillation, 202.4 g of a mixture were recovered.

By fractionating distillation 98.3 g of dioxolane (11) and 81.1 g of $CFCl_2CFCl_2$ were collected.

The dioxolane (11) yield, defined as in example 1, was of 66%

We claim:

1. Halogenated 1,3-dioxolanes of formula:

in which:

$X_1$, $X_2$, $X_3$ and $X_4$, like or different from one another, represent F, Cl, Br, I, $CF_2OSO_2F$, $SO_2F$, $C(O)F$, H, perhaloalkyl or oxyperhaloalkyl radicals containing from 1 to 5 carbon atoms; $X_5$ is F and $X_6$ is F or $CF_3$;

at least one from among $X_1$, $X_2$, $X_3$, $X_4$ is Br, I, $CF_2OSO_2F$, $SO_2F$, $C(O)F$ or an oxyperhaloalkyl radical containing from 1 to 5 carbon atoms, and that when one from among $X_1$, $X_2$, $X_3$ and $X_4$ is Br or I, the other three are F.

2. Halogenated 1,3-dioxolanes according to claim 1, wherein at least two out of $X_1$, $X_2$, $X_3$ and $X_4$ are F.

3. Halogenated 1,3-dioxolanes according to claim 1, wherein at least three out of $X_1$, $X_2$, $X_3$ and $X_4$ are F.

4. Halogenated 1,3-dioxolanes according to claim 1, wherein $X_6$ is F.

5. Halogenated 1,3 dioxolanes of formula:

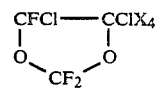

wherein $X_4$ is a perfluoroalkyl radical containing from 1 to 5 carbon atoms.

* * * * *